United States Patent [19]

Mikkelsen

[11] Plant 4,191

[45] Jan. 17, 1978

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 764,011

[22] Filed: Jan. 31, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Donald D. Jeffery

[57] ABSTRACT

A novel Impatiens plant having white blossoms and large, variegated leaves.

1 Drawing Figure

1

The present invention relates to a new and distinctive cultivar of Impatiens plant, botanically known as Impatiens and known by the cultivar name Patriot. The new cultivar was developed by me through controlled breeding by crossing the unpatented seedling 74-136-1 (Mikkelsen) (seed parent) with the unpatented seedling 74-211-2 (Mikkelsen) (pollen parent). Asexual reproduction of terminal or stem cuttings has shown that the unique features of this new Impatiens are stabilized and are reproduced true to type in successive propagations.

The following characteristics distinguish the new Impatiens from both its parent varieties and other cultivated Impatiens of this type known and used in the floriculture industry:

1. Distinctive white flower at maturity, up to 6 cm. in diameter. Flowers are held close or tight to the foliage.
2. Large variegated foliage, close internodes.
3. Slow growing, thereby providing pot plant potential.
4. A companion to my white Impatiens cultivar Monticello, but having less clear cut leaf variegation; Patriot does not present as many flowers in bloom at one time as does Monticello, which is disclosed in my application Ser: No. 764,012 filed Jan. 31, 1977.
5. Compact habit, which tends to restrict rapid development of side growth so that cutting production is somewhat less than other cultivars resulting from the breeding program.

The accompanying colored photograph illustrates the overall appearance of this cultivar taken as a top view of the plant and showing the colors as true as it is reasonably possible to obtain in a colored reproduction of this type. The plant illustrated was grown in a 5" clay pot without removal of apical tip.

The following is a detailed description of my new Impatiens cultivar based on plants produced under commercial practices in the greenhouses of Mikkelsens Inc., Ashtabula, Ohio during September, 1975. Color references are made to the Royal Horticultural Society Colour Chart except where general terms of ordinary dictionary significance are used.

Parentage: A controlled pollination of Mikkelsen seedling 74-136-1 as the seed parent crossed with Mikkelsen seedling 74-211-2 as the pollen parent.

Propagation:

*Type cutting.*—Tip cuttings 2–3 cm. long.

*Time to visible rooting.*—10–12 days at 21° C summer, and 12–16 days at 20° winter.

2

*Rooting habit.*—Considered rapid, profuse with both primary and secondary roots, dendritic pattern.

Plant description:

*Form.*—Vigorous, upright, extremely close internodes, herb.

*Habit of growth.*—Upright, compact, slow growing, self branching.

*Foliage.*—Abundant, well textured, dark green with pronounced variegation; Size: Up to 6 cm. wide and up to 15 cm. long, with petioles up to 4–5 cm. long; Shape: symmetrically elliptical, strongly revolute; apice acute, base acute, Texture: Leathery, glabrous, rugose; Margin: Nearly entire, finely cilioate; Color: Mature foliage: Top side: Outer margin darker than yellow green 147-A, inner area near yellow 11C; Under side: Outer margin between 147 yellow green A, B, inner area yellow 11C-D. Young foliage: Very similar in color to mature foliage except the degree of variegation. Venation: Pinnately, arcuate.

Flowering description:

*Flowering habits.*—Flowering appears to be sparse, because flower development is slow and older flowers have deteriorated, less than one flower per leaf.

*Natural flowering season.*—Flowering is indeterminate; however plants tend to be more floriferous in winter than summer.

*Flower buds.*—Typically symmetrically conical, covered with 2 distinct sepals and a scale-like sepal on the back side of the top petals; as bud develops the spur curves outward from the bottom.

*Flowers borne.*—Single blooms supported on a short near colorless pedicel 3–4 cm. long by 1.5 mm., to 2 mm. in diameter at base; pedicel does not elongate so that flowers are held close to the foliage.

*Quantity of flowers.*—Generally less by 25–30% than most of the New Guinea hybrids.

*Petals.*—Shape: Generally heartshaped, apex notched. Color: Top side in winter when opening, very soft flush of pink, fading to white; under side white. Number of petals: 5; top petal largest, bottom 2 intermediate in size, side 2 smallest. Size of petals: Top petal up to 3 cm; flower diameter up to 6 cm.

*Reproductive organs.*—Stamens: one in number; Anther shape: Hooded over pistil; Color: white; Pollen: Color White; Pistils: Stigma: flat, shape circular, irregular surface; color, green crystalline; Style: Color, translucent to green. Ovaries: One in number; size 3–4 mm. green in color.

I claim:

1. A new and distinct cultivar of Impatiens plant known by the cultivar name Patriot and particularly characterized as to uniqueness by the combined characteristics of distinct white flower color at maturity, with the flower being close to the foliage; large variegated foliage with close internodes, and slow growth and compact habit.

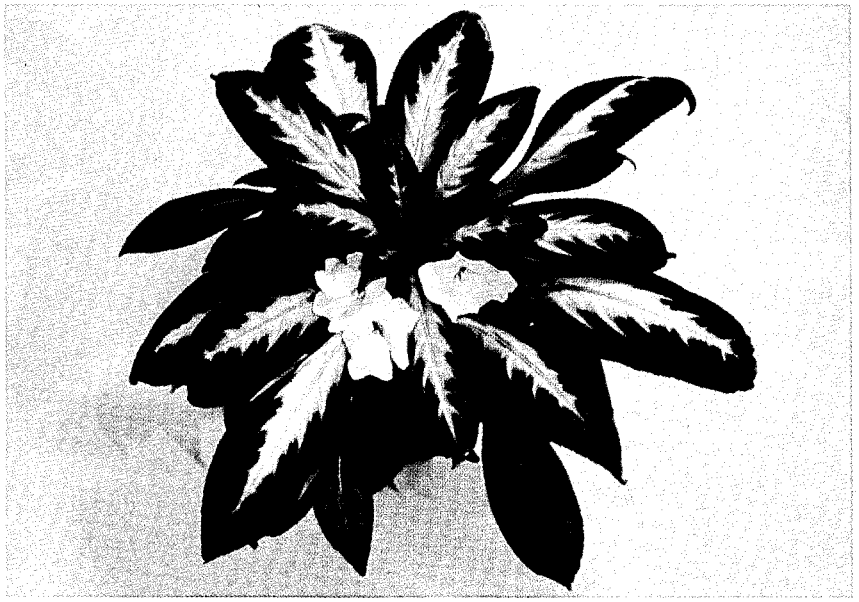

* * * * *